(12) United States Patent
Qin

(10) Patent No.: US 6,608,215 B2
(45) Date of Patent: Aug. 19, 2003

(54) OXYGEN-CONTAINING HETEROCYCLIC FUSED NAPHTHOPYRANS

(75) Inventor: Xuzhi Qin, Hacienda Heights, CA (US)

(73) Assignee: Vision-Ease Lens, Inc., Ramsey, MN (US)

( * ) Notice: Subject to any disclaimer, the term of this patent is extended or adjusted under 35 U.S.C. 154(b) by 0 days.

(21) Appl. No.: 09/957,403

(22) Filed: Sep. 20, 2001

(65) Prior Publication Data

US 2003/0092918 A1 May 15, 2003

(51) Int. Cl.[7] .................... C07D 311/78; C07D 487/02; C03C 8/00; G02B 3/00; G02F 1/03
(52) U.S. Cl. .................. 549/383; 549/384; 501/13; 359/241; 359/244
(58) Field of Search ................ 549/383, 384; 359/241, 244; 501/13

(56) References Cited

U.S. PATENT DOCUMENTS

| | | | |
|---|---|---|---|
| 565,123 A | 8/1896 | Scott | |
| 3,567,605 A | 3/1971 | Becker | 204/158 |
| 3,627,690 A | 12/1971 | Casella et al. | 252/300 |
| 4,826,977 A | 5/1989 | Heller et al. | 544/70 |
| 5,200,116 A | 4/1993 | Heller | 252/586 |
| 5,238,981 A | 8/1993 | Knowles | 524/110 |
| 5,411,679 A | 5/1995 | Kumar | 252/586 |
| 5,429,744 A | 7/1995 | Hagqvist | 210/493.1 |
| 5,451,344 A | 9/1995 | Knowles et al. | 252/586 |
| 5,458,814 A | 10/1995 | Kumar et al. | 252/586 |
| 5,645,767 A | 7/1997 | Van Gemert | 252/586 |
| 5,651,923 A | 7/1997 | Kumar et al. | 252/586 |
| 5,674,432 A | 10/1997 | Knowles et al. | 252/586 |
| 5,698,141 A | 12/1997 | Kumar | 252/586 |
| 5,783,116 A | 7/1998 | Lin | 252/586 |
| 6,018,059 A | 1/2000 | Chan | 549/382 |
| 6,210,608 B1 | 4/2001 | Chan et al. | 252/586 |
| 6,348,604 B1 | 2/2002 | Nelson et al. | 549/389 |

FOREIGN PATENT DOCUMENTS

| WO | WO 95/05382 | 2/1995 | C07D/491/04 |
|---|---|---|---|
| WO | WO 96/14596 | 5/1996 | G02B/5/23 |
| WO | WO 97/21698 | 6/1997 | C07D/311/78 |
| WO | WO 00/15628 | 3/2000 | C07D/311/92 |

*Primary Examiner*—Taofiq Solola
(74) *Attorney, Agent, or Firm*—Mark A. Litman & Assoc. P.A.

(57) ABSTRACT

Novel naphthopyrans having an oxygen-containing heterocyclic group F annelated on the f, i, j, or k side of the naphthopyran ring. These naphthopyrans may have the formula (I) presented below:

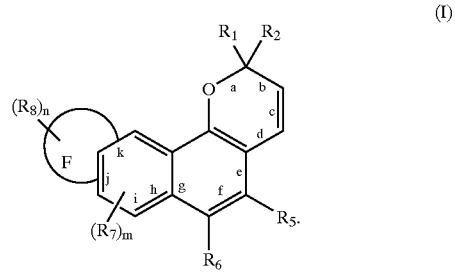

These compounds (I) have interesting photochromic properties. Various organic host materials that contain such compounds are described. Articles such as ophthalmic lenses or other plastic transparencies that incorporate the novel naphthopyran compounds or combinations are enabled.

44 Claims, No Drawings

OXYGEN-CONTAINING HETEROCYCLIC FUSED NAPHTHOPYRANS

BACKGROUND OF THE INVENTION

1. Field of the Invention

The present invention relates to novel naphthopyran-type compounds that have, in particular, photochromic properties. The invention also relates to photochromic compositions and photochromic ophthalmic articles (goggles, lenses and eye-shields, for example) that contain these naphthopyrans. The invention also covers the preparation of these novel naphthopyrans. The photochromic compounds are capable of changing color under the influence of a first poly- or mono-chromatic light (UV for example) and of returning to their initial color when the luminous irradiation ceases, or under the influence of temperature and/or poly- or mono-chromatic light different from the first light. The invention particularly relates to naphthopyrans having an Oxygen-containing heterocyclic group fused to the naphthopyran.

2. Background of the Art

Photochromism generally concerns the ability of a compound to reversibly change color under different light conditions. One particular type of photochromic phenomenon concerns the reversible change in color of a compound from an original color to a different color when the compound is exposed to a source of ultraviolet radiation, such as solar radiation or light radiated from a mercury or xenon lamp. The photochromic compound fades to the original color within a period of time after the photochromic compound is isolated from the ultraviolet radiation, such as by placing the compound in a dark room.

Photochromic compounds find applications in various fields, such as for the manufacture of ophthalmic lenses, contact lenses, solar protection glasses, goggles, sun screens, filters, camera optics, photographic apparatus optics or other optical devices and observation devices, glazing, decorative objects, currency elements and even for information storage by optical inscription (coding). For example, photochromic compounds, such as naphthopyrans, are incorporated into plastic ophthalmic lenses to effect color changes in the lenses when the lenses are exposed to particular lighting conditions. Additionally, different photochromic compounds may be blended together to create a color effect that is different from respective color effects of the individual photochromic compounds. As an example, a first photochromic compound that turns orange or red when activated by light and a second photochromic compound that turns blue when activated by light may be blended together to form a photochromic mixture that produces a shade of gray when activated by light.

In the field of ophtalic optics, and in particular the field of spectacles, a photochromic lens that comprises one or more photochromic compounds is usually required to have:

- a high transmission level in the visible region in the absence of ultraviolet radiation,
- a low transmission (high colorability) under solar irradiation (especially with ultraviolet exposure),
- desired coloration and discoloration kinetics, e.g., high sensitivity to irradiation and fast bleaching,
- a high solubility in hosting materials,
- a tint acceptable to the consumer (gray or brown preferably) with the chosen tint maintained during the coloration and the discoloration of the lens,
- a maintenance of the performance and properties, within a temperature range of 0–40° C.,
- a significant durability, since these objectives sought after are used in sophisticated corrective lenses and are therefore expensive.

These lens characteristics are primarily determined by the active photochromic compounds. These compounds must furthermore be compatible with the organic or inorganic support that constitutes the lens.

Moreover, it is to be noted that obtaining a neutral gray or brown tint may necessitate the use of at least two photochromes of different colors, i.e., two separate compounds having distinct maximal absorption wavelengths in the visible region of the electromagnetic spectrum. The use of combinations of photochromic compounds imposes other requirements on both the individual photochromic compounds and the groups of photochromic compounds. In particular, the coloration and discoloration kinetics of the (two or more) combined active photochromic compounds must be essentially identical. The same applies for their stability with time, and also for their compatibility with a single plastic or inorganic support.

Amongst the numerous photochromic compounds described in the prior art, benzopyrans or naphthopyrans are described in patents or patent applications U.S. Pat. Nos. 3,567,605; 3,627,690; 4,826,977; 5,200,116; 5,238,981; 5,411,679; 5,429,744; 5,451,344; 5,458,814; 5,651,923; 5,645,767; 5,698,141; WO-A-95 05382; WO-A-96-14596; WO-A-97 21698 which are of the reduced formula below:

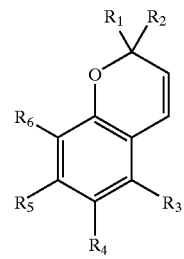

U.S. Pat. Nos. 5,651,923 and 6,018,059 more specifically describe naphthopyrans having benzofurano or naphthofurano groups fused to the naphthalene ring of naphthopyran (the general structures are shown below).

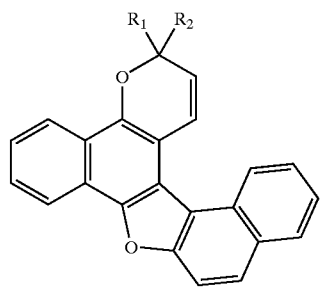

U.S. Pat. No. 5,651,923

-continued

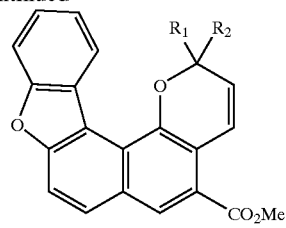

U.S. Pat. No. 5,651,923

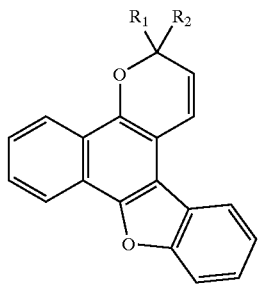

U.S. Pat. No. 6,018,059

The various substitutent groups are defined in the various patents and encompass a wide, art-accepted range of combinations of substitutents intended to provide specific physical or photochromic properties. These compounds claim to satisfy the specifications identified above as needed for photochromic compounds. In reality, even if these compounds really do have one or more of the basic properties sought after, such as a high transmission in the absence of ultraviolets and a high colorability under solar irradiation, none of the compounds described hitherto have the complete combination of properties necessary for the production of satisfactory articles. In particular, none of these compounds is intrinsically gray or brown, and the necessity of using an additional photochromes in order to obtain one of these two tints does subsist.

SUMMARY OF THE INVENTION

A novel family of molecules is described having particularly advantageous photochromic properties, such as, two intense absorption bands in the visible range and absorption bands that cover a significant part of visible spectrum (400–700 nm). This novel type of compound adapts or blends well in association with red and/or yellow complementary photochromes to give brown or gray tints.

According to a first aspect of the invention is described Naphthopyran having a central nucleus of the formula:

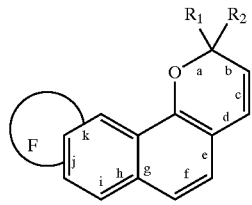

wherein F is an oxygen-containing 5- to 7-member heterocyclic ring group, its 2,3 or 3,2 positions fused to the f, i, j, or k side of the ring, and $R_1$ and $R_2$ are the atoms or groups providing photochromic properties to the naphthopyran.

This naphthopyran may preferably have $R_1$ is selected from the group consisting of a hydrogen, a linear or branched alkyl group of 1 to 12 carbon atoms, a cycloalkyl group of 3 to 12 carbon atoms, an aryl group of 6 to 24 ring carbon atoms or a heteroaryl group of 4 to 24 carbon atoms and at least one hetero ring atom selected from sulfur, oxygen and nitrogen; and wherein $R_1$ and $R_2$ together form an adamantyl, norbornyl, fluorenylidene, di(C1–C6) alkylanthracenylidene or spiro(C5–C6) cycloalkylanthracenylidene group.

Another aspect is a naphthopyran having the central nucleus of the formula:

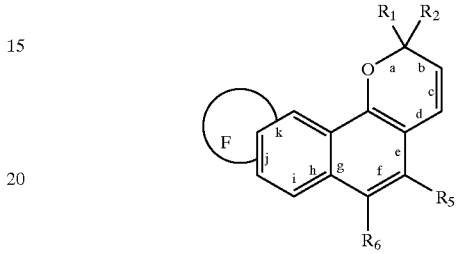

wherein F is an oxygen-containing 5- to 7-member heterocyclic ring group, its 2,3 or 3,2 positions fused to the f, i, j, or k side of the ring, and $R_1$ and $R_2$ are the atoms or groups necessary to provide photochromic properties to the naphthopyran and $R_5$ and $R_6$ are selected from the group consisting of:
a hydrogen,
a halogen,
a linear or branched alkyl group of 1 to 12 carbon atoms,
a cycloalkyl group of 3 to 12 carbon atoms,
a linear or branched alkoxy group of 1 to 12 carbon atoms,
a linear or branched alkenyl or alkynyl group of 1–12 carbon atoms,
a linear or branched alkenyloxy or alkynyloxy group of 1–12 carbon atoms,
an aryl or heteroaryl group, and
an aralkyl or heteroaralkyl group, the alkyl group, which is linear or branched, of 1 to 4 carbon atoms.

According to another aspect of the present invention, naphthopyran compounds of the following formula (I) are described and enabled:

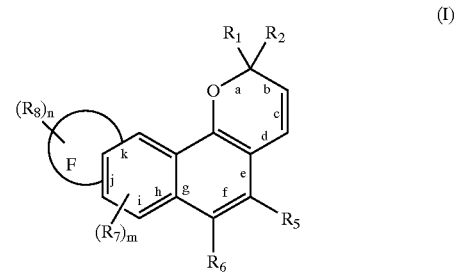

(I)

in which:
F is an at least one oxygen-containing, 5- to 7-member heterocyclic ring group with or without substitutions. Its 2,3 or 3,2 positions are fused to the f, i, j, or k side of the naphthopyran as identified in Formula (I);

$R_1$ and $R_2$, for example, may independently represent:
a hydrogen, a linear or branched alkyl group which comprises 1 to 12 carbon atoms (with or without substitution), a cycloalkyl group which comprises 3 to 12 carbon atoms, an aryl or heteroaryl group which comprises in its basic structure (that is, in its ring atoms, the rings comprising 5, 6 or 7 atoms) 6 to 24 carbon atoms or 4 to 24 carbon atoms respectively and at least one heteroatom selected from sulfur, oxygen and nitrogen; the basic structure being optionally substituted with at least one substituent selected from:

a halogen atom (e.g., fluorine, chlorine and bromine), a hydroxy group, a linear or branched alkyl group comprising 1 to 12 carbon atoms, a linear or branched alkoxy group comprising 1 to 12 carbon atoms, a haloalkyl or haloalkoxy group corresponding to the ($C_1$–$C_{12}$) alkyl or alkoxy groups above respectively which are substituted with at least one halogen atom, and notably a fluoroalkyl group of this type, a linear or branched alkenyl group comprising 2 to 12 carbon atoms, and notably a vinyl group or an allyl group, an —$NH_2$ group, an —$NHR_{11}$ group, $R_{11}$ representing a linear or branched alkyl group comprising 1 to 6 carbon atoms, a

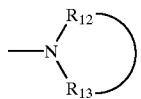

group, in which $R_{12}$ and $R_{13}$, which are the same or different, independently representing a linear or branched alkyl group comprising 1 to 6 carbon atoms, or representing (together with the nitrogen atom to which they are bound) a 5- to 7-membered ring which can comprise at least one other heteroatom selected from oxygen, sulfur and nitrogen, said nitrogen being optionally substituted with an $R_{14}$ group, which is a linear or branched alkyl group comprising 1 to 6 carbon atoms, a methacryloyl group or an acryloyl group, an aralkyl or heteroaralkyl group, the alkyl group, which is linear or branched, comprising 1 to 4 carbon atoms and the aryl and heteroaryl groups having the definitions given above, or the two substituents R1 and R2 together forming ring group such as those represented by an adamantyl, norbornyl fluorenylidene, 5,5- or 10,10-di(C1–C6) alkylanthracenylidene, 5 (or 10)-(C1–C6)alkyl-5 (or 10)-OH (or $OR_{15}$)anthracenylidene or spiro(C5–C6) cycloalkylanthracenylidene ring group; said ring group being optionally substituted with at least one of the substituents listed above in the definitions for $R_1$, $R_2$; said ring group being optionally substituted with two adjacent groups that form a 5- to 6-member aromatic or non-aromatic ring which can comprise at least one heteroatom selected from oxygen, sulfur, and nitrogen.

$R_5$ and $R_6$ are identical or different and they represent, independently:

a hydrogen, a halogen, and notably fluorine, chlorine or bromine, a linear or branched alkyl group which comprises 1 to 12 carbon atoms (advantageously 1 to 6 carbon atoms), a cycloalkyl group comprising 3 to 12 carbon atoms, a linear or branched alkoxy group comprising 1 to 12 carbon atoms (most advantageously 1 to 6 carbon atoms), a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine, a linear or branched alkenyl or alkynyl group comprising 1–12 carbon atoms, preferably a vinyl or allyl group, a linear or branched alkenyloxy or alkynyloxy group comprising 1–12 carbon atoms, preferably an allyloxy group, an aryl or heteroaryl group having the same definition as that given above for aryl or heteroaryl groups within the definitions of $R_1$, $R_2$, an aralkyl or heteroaralkyl group, the alkyl group, which is linear or branched, comprising 1 to 4 carbon atoms, and the aryl and heteroaryl groups having the same definitions as those given above for $R_1$, $R_2$, an amine or amide group: —$NH_2$, —$NHR_{11}$, —$CONH_2$, —$CONHR_{11}$,

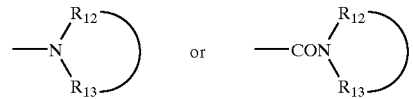

$R_{11}$, $R_{12}$, and $R_{13}$ having their respective definitions given above for the amine substituents of the values $R_1$, $R_2$, a —$C(R_{16})_2X$ group, wherein X is —CN, halogen, hydroxy, alkoxy, benzoyloxy, C1–C6 acyloxy, amino, C1–C6 mono-alklamino, C1–C6 dialkyl amino, morpholino, piperidino, 1-indolinyl, pyrrolidyl, or trimethylsilyloxy, $R_{16}$ is hydrogen, C1–C6 alkyl, phenyl or naphthyl with C1–C6 alkyl or C1–C6 alkoxy substituents, an —$OCOR_{17}$ or —$COOR_{17}$ group, $R_{17}$ representing a straight or branched alkyl group comprising 1 to 6 carbon atoms, or a cycloalkyl group comprising 3 to 6 carbon atoms, or a phenyl group, optionally substituted with at least one of the substituents listed above within the values in the definitions of $R_1$, $R_2$, a methacryloyl group or an acryloyl group, an epoxy group having the formula,

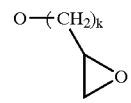

in which k=1, 2 or 3, $R_5$ and $R_6$ together form a 5- to 7-member aromatic or non-aromatic ring which can comprise at least one heteroatom selected from oxygen, sulfur, and nitrogen, and/or at least one substituent selected from the group consisting of a C1 to C6 alkyl gou which is linear or bracnched, a C1 to C6 alkoxy group which is linear or branched, and an amine group of formula —NH2, NHR$_{11}$, or

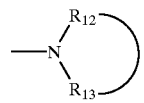

as defined in R$_1$ and R$_2$ for amine groups,
a polyether, polyamide, polycarbonate, polycarbamate, polyurea or polyester residue;

each R$_7$ group can be same or different, independently representing
a hydrogen, a halogen, and notably fluorine, chlorine or bromine,
a linear or branched alkyl group which comprises 1 to 12 carbon atoms (advantageously 1 to 6 carbon atoms),
a cycloalkyl group comprising 3 to 12 carbon atoms,
a linear or branched alkoxy group comprising 1 to 12 carbon atoms (advantageously 1 to 6 carbon atoms),
a haloalkyl, halocycloalkyl, or haloalkoxy group corresponding to the alkyl, cycloalkyl, alkoxy groups described above respectively, which are substituted with at least one halogen atom, notably selected from fluorine, chlorine and bromine,
a linear or branched alkenyl or alkynyl group comprising 1–12 carbon atoms, preferably a vinyl or allyl group,
a linear or branched alkenyloxy or alkynyloxy group comprising 1–12 carbon atoms, preferably a allyloxy group,
an aryl or heteroaryl group having the same definition as that given supra for R$_1$, R$_2$,
an aralkyl or heteroaralkyl group, the alkyl group, which is linear or branched, comprising 1 to 4 carbon atoms, and the aryl and heteroaryl groups having the same definitions as those given above for R$_1$, R$_2$,
an amine or amide group, such as —NH$_2$, —NHR$_{11}$, —CONH$_2$, —CONHR$_{11}$,

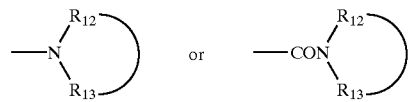

R$_9$, R$_{10}$, and R$_{12}$ having their respective definitions given above for the amine substituents and for the definitions of R$_1$, R$_2$,
a —C(R$_{16}$)$_2$X group, wherein X is —CN, halogen, hydroxy, alkoxy, benzoyloxy, C1–C6 acyloxy, amino, C1–C6 mono-alklamino, C1–C6 dialkyl amino, morpholino, piperidino, 1-indolinyl, pyrrolidyl, or trimethylsilyloxy, R$_{16}$ is hydrogen, C1–C6 alkyl, phenyl or naphthyl with C1–C6 alkyl or C1–C6 alkoxy substituents,
an —OCOR$_{17}$ or —COOR$_{17}$ group, R$_{17}$ representing a straight or branched alkyl group comprising 1 to 6 carbon atoms, or a cycloalkyl group comprising 3 to 6 carbon atoms, or a phenyl group, optionally substituted with at least one of the substituents listed above for the values of R$_1$, R$_2$: aryl or heteroaryl,
a methacryloyl group or an acryloyl group, an epoxy group having the formula,

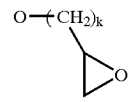

in which k=1, 2 or 3,
a polyether, polyamide, polycarbonate, polycarbamate, polyurea or polyester residue,
m is an integer from 0 to 2;
each R$_8$ group can be the same or different, independently representing
a hydrogen,
a halogen, and notably fluorine, chlorine or bromine,
a linear or branched alkyl group which comprises 1 to 12 carbon atoms (advantageously 1 to 6 carbon atoms),
a cycloalkyl group comprising 3 to 12 carbon atoms,
two of the R$_8$ groups, which are adjacent or bonded to the same carbon atom in the group F, form a 5- to 7-membered non-aromatic ring which can comprise at least one heteroatom selected from the group consisting of oxygen, sulfur, and nitrogen,
n is an integer from 0 to 4.

The terms "group" and "central nucleus" have established meanings according to the practice of the present invention. Where the term "group" is used, the chemical unit described is intended to include and allow for substituents consistent with the primary chemical unit. For example, where the term alkyl group is used, that term is intended to include classic alkyl materials such as methyl, ethyl, propyl, butyl, hexyl, octyl, iso-octyl, dodecyl, cyclohexyl and the like, and is also intended to include alkyl units with substitution thereon consistent with the underlying nature of an alkyl unit, such as hydroxymethyl, bromoethyl, dichloropropyl, 1,2,3,4-tetrachlorobutyl, omega-cyanohexyl and the like. Where the term "alkyl moiety" is used, no substitution is allowed.

The terminology of a central nucleus of a provided formula has a similar meaning. The term indicates that the formula, even though atoms are shown in the formula, may be substituted with any chemical units as long as the underlying bond structure of the formula is not altered. For example, where the term a central nucleus of the formula

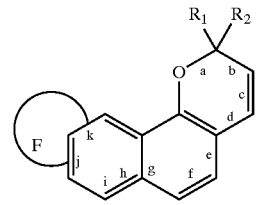

is used, there may be any substitution at such positions as 3, 4, 5, 6, 7, 8, 9, or 10 as long as the structure of F is not destroyed and the bond structure shown (e.g., the double bonds) are not converted to single bonds (e.g., by attempting to provide two substituents at the 6-position, which would require elimination of the double bond between positions 5 and 6. Where the term a compound of the formula is used, except for description of the term 'group' in definitions, no unspecified substitution is allowed.

Where the term 'group' or 'central nucleus' is used in the practice of the present invention, those terms refer to the capability of the structure to have substitution or not on the chemical unit or not. The term 'group' refers to any chemical structure, while the term 'central nucleus' refers specifically to a ring structure as the core chemical moiety. For example, an 'alkyl group' includes unsubstituted n-alkyl, iso-alkyl, methyl ethyl, octyly, iso-octyl, docecyl, and the like, and substituted alkyl such as hydroxymethyl, 1-chloroethyl, 2-cyano-butyl, 3-ethyl-4-hexyl, omega-carboxy-pentyl, and the like. Where the term 'moiety' is used, as in the term alkyl moiety is used, that term refers to only unsubstituted chemical units. Similarly, where the term 'central nucleus' is used, such as in the central nucleus of a naphthyl, any substituent may be present on the central nucleus of the naphthyl group, such as 1-methyl-, 2-chloro-, 2,4-dimethoxy-, 2,2'-dimethoxy-, and the like. Where the term having a structure of the specific formula is used, no substitution is allowed beyond that of the described formula.

Among the substituents that can be considered for the compounds of formula (I) according to the invention, groups should be considered that comprise and/or form at least one function which can be polymerized and/or crosslinked, which group are preferably selected from the following list: alkenyl, advantageously vinyl, methacryloyl, acryloyl, acryloxyalkyl, methacryloxyalkyl or epoxy.

Thus, the photochromic compounds according to the invention can be monomers, of different types or not, that can react with each other or with other comonomers to form homopolymers and/or copolymers that bear a photochromic functionality and possess mechanical properties of macromolecules. It follows that one of the objects of the present invention consists of these homopolymers or copolymers comprising (co)monomers and/or of crosslinked compounds, that, at least in part, consist of photochromic compounds (I) according to the invention.

In the same general concept, the above-mentioned compounds (I) can be crosslinking agents that have one or more reactive functions capable of allowing the formation of bridges between chains of polymers of photochromic nature or not. The crosslinked compounds that can be obtained in this manner also are a part of the present invention.

Amongst such compounds according to formula (I), preferred photochromic are those which have the formula (Ia), (Ib), (Ic), and (Id) below:

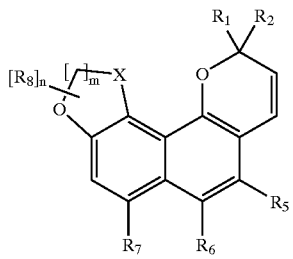

(Ia)

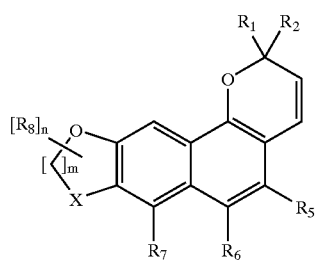

(Ib)

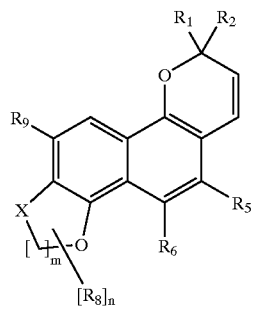

(Ic)

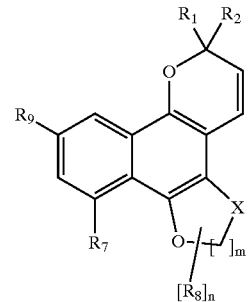

(Id)

in which:

X is a carbon or oxygen atom, m is an integer 1 or 2, $R_1$ and/or $R_2$, independently represent optionally substituted aryl or heteroaryl groups the basic structure of which is selected from those of phenyl, naphthyl, biphenyl, pyridyl, furyl, benzofuryl, dibenzofuryl, N—$(C_1-C_6)$alkylcarbazole, thienyl, benzothienyl, dibenzothienyl, julolidinyl groups; $R_1$ and/or $R_2$ advantageously representing a para-substituted phenyl group or $R_1$ and $R_2$ together form an adamantyl group or norbornyl group or anthracenylidene group;

$R_5$ and $R_6$ are the same or different, and may represent independently a hydrogen, a linear or branched alkyl group that comprises 1 to 6 carbon atoms, a —$C(R_{16})_2X$ group, wherein X is hydroxy, alkoxy, benzoyloxy, C1–C6 acyloxy, an amine or amide group: —$NH_2$, —$NHR_{11}$, —$N(R_{11})_2$, —$CONH_2$, —$CONHR_{11}$, —$CON(R_{11})_2$, $R_{16}$ is hydrogen, C1–C6 alkyl, phenyl or naphthyl with C1–C6 alkyl or C1–C6 alkoxy substituents, an optionally substituted phenyl or benzyl group, a —$COR_{17}$, or —$COOR_{17}$ group, $R_{17}$ representing a linear or branched alkyl group comprising 1 to 6 carbon atoms, or $R_5$ and $R_6$ together form a 5- to 7-member aromatic or non-aromatic ring which can comprise at least one heteroatom selected from oxygen, sulfur, and nitrogen, and/or at least one substituent selected from the group consisting of a C1 to C6 alkyl gou which is linear or bracnched, a C1 to C6 alkoxy group which is linear or branched, and an amine group of formula —NH2, NHR₁₁, or

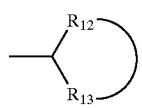

as defined in $R_1$ and $R_2$ for amine groups;

$R_7$ and $R_9$ are the same or different, and may represent independently
- a hydrogen,
- a halogen, and notably fluorine, chlorine or bromine,
- a linear or branched alkyl group which comprises 1 to 12 carbon atoms (advantageously 1 to 6 carbon atoms),
- a cycloalkyl group comprising 3 to 12 carbon atoms,
- a linear or branched alkoxy group comprising 1 to 12 carbon atoms (advantageously 1 to 6 carbon atoms),
- a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
- a linear or branched alkenyl or alkynyl group comprising 1–12 carbon atoms, preferably a vinyl or allyl group,
- a linear or branched alkenyloxy or alkynyloxy group comprising 1–12 carbon atoms, preferably a allyloxy group,
- an aryl or heteroaryl group having the same definition as that given supra for $R_1$, $R_2$,
- an aralkyl or heteroaralkyl group, the alkyl group, which is linear or branched, comprising 1 to 4 carbon atoms, and the aryl and heteroaryl groups having the same definitions as those given supra for $R_1$, $R_2$,
- an amine or amide group: $-NH_2$, $-NHR_{11}$, $-NR_{12}R_{13}$, $R_{11}$, $R_{12}$, $R_{13}$ having their respective definitions given supra for the amine substituents of the values $R_1$, $R_2$, $R_{12}$ and $R_{13}$ can form a saturated or unsaturated ring with or without substituents;

$R_8$, which are identical or different, represent, independently
- a hydrogen,
- a linear or branched alkyl group which comprises 1 to 12 carbon atoms (advantageously 1 to 6 carbon atoms),
- a cycloalkyl group comprising 3 to 12 carbon atoms,
- a $-C(R_{16})_2X$ group, wherein X is hydroxy, C1–C6 alkoxy, benzoyloxy, C1–C6 acyloxy, an amine or amide group: $-NH_2$, $-NHR_{11}$, $-NR_{12}R_{13}$, $R_{11}$, $R_{12}$, $R_{13}$ having their respective definitions given supra for the amine substituents of the values $R_1$, $R_2$, $R_{12}$ and $R_{13}$ can form a saturated or unsaturated ring with or without substituents, $R_{16}$ is hydrogen, C1–C6 alkyl, phenyl or naphthyl with C1–C6 alkyl or C1–C6 alkoxy substituents, These compounds present particularly advantageous photochromic properties, such as, having strong coloration ability with two absorption bands in the visible range with high $\lambda_{max}$ values. These compounds are also preferably stable and compatible with matrices made of at least one organic polymer or mineral material (e.g., inert inorganic binder), both in the form included in the matrix and in the form of a coating.

In a solution or in the polymer matrix, the compounds according to the invention are colorless or slightly colored in the initial state and they rapidly develop an intense coloration under UV light (365 nm) or a luminous source of the solar type. They rapidly recover their initial color when the irradiation stops.

General Synthetic Procedure for Preparation of the Compounds

The compounds of the invention can be obtained by the condensation of a derivative of 1-naphthol that is suitably substituted and a derivative of propargyl alcohol. The condensation can be carried out in organic solvents, particularly non-polar solvents such as toluene, xylene or tetrahydrofuran and, optionally, in the presence of a catalyst, acid catalysts, and especially acid catalysts such as fluorinated organic acid catalysts, p-toluenesulfonic acid, chloroacetic acid or acid aluminic acid):

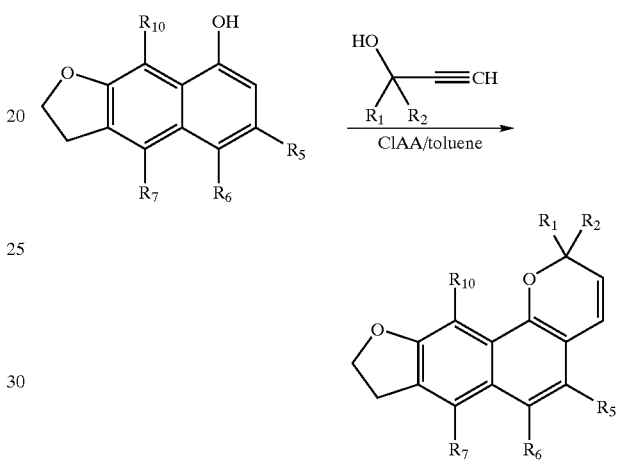

These synthetic routes are classical and have been described in the above-mentioned references of the prior art as well as in U.S. Pat. No. 4,818,096. The propargyl alcohols are either commercially available or easily synthesized by the reaction of lithium acetylide or ethynyl (magnesium bromide) with the corresponding ketones $(R_1)CO(R_2)$. The ketones are also either commercially available or easily synthesized by the classical methods, for example, the Friedel-Crafts reaction from an acid chloride.

The derivatives of 1-naphthol are obtained by various methods adapted from the literature. Below we give some references on methods that allow the synthesis of the compounds of the invention.

Method 1: Johnson et al. Org. React. 1951, Vol. 6, p. 1.

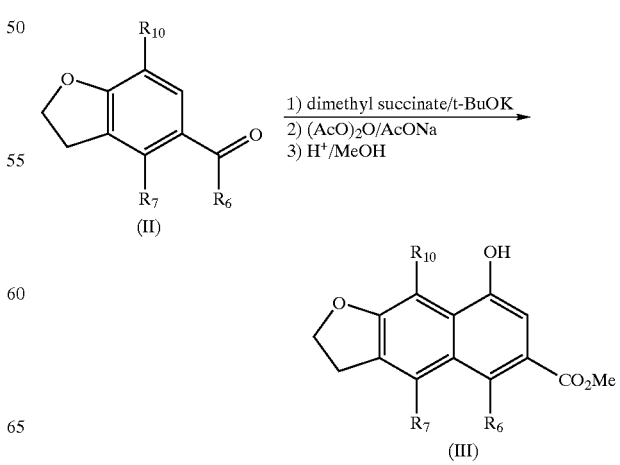

Method 1a:

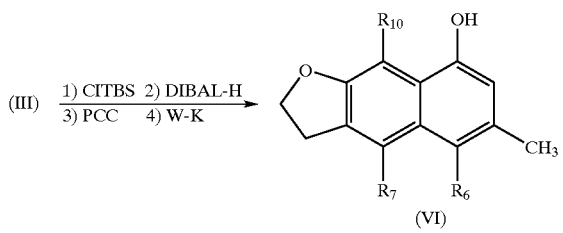

Method 1b:

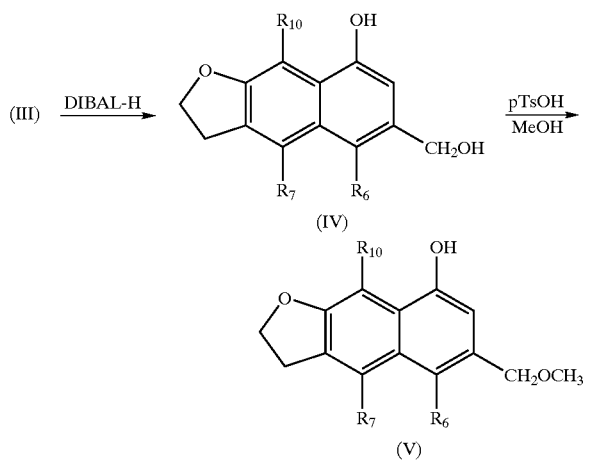

Method 2: U.S. Pat. No. 5,200,116 (Example 2) or U.S. Pat. No. 6,207,084

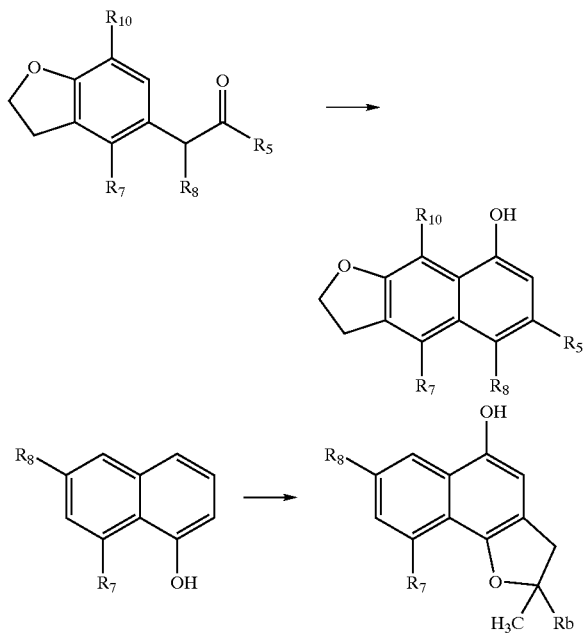

Method 3: Cameron et al., *Aust. J. Chem.*, 1983, 35, p1481

DIBAL-H: diisobutoxyaluminum hydride, pTsOH: p-toluenesulphonic acid, MeOH: methanol, CITBS: chlorodimethyl-t-butyl silane, PCC: pyridium chlorochrome, W-K: Wolff-Kishiner reduction.

The starting aldehyde in Method 1 can be prepared according to the route described in B. J. Bradbury, etal., *J. Heterocyclic Chem.*, 26, 1827 (1989), and the starting ketone in Method 2 can be prepared according to the procedure in U.S. Pat. No. 6,210,608. Aromatic aldehydes can also be prepared through the Vilsimeier formylation (cf. Vilsmeier, A.; Haack, A. *Ber.*, 1927, 60, 119)

Regarding the commercial application of compounds according to the present invention, it should be noted that they can be used as a photochromic material dispersed in the composition of a polymer matrix. They can also be used in solution.

A photochromic solution can be obtained by dissolving the compound in an organic solvent, such as toluene, dichloromethane, tetrahydrofuran or ethanol. The solutions obtained are generally colorless and transparent. When exposed to sunlight, they develop a strong coloration and they recover the color of this state when placed in an environment with lesser exposure to solar radiation or, in other words, when they are no longer exposed to UV radiation. In general, a very low concentration of products (on the order of 0.01–5% by weight or volume) is sufficient to obtain an intense coloration.

The most interesting applications are those in which the photochrome is dispersed uniformly within or on the surface of a polymer, copolymer or mixture of polymers. The implementation methods that can be considered are of a great variety. Among those known to a person skilled in the art, one can cite, for example, diffusion in the (co)polymer, from a suspension or solution of the photochrome, in a silicone oil, in an aliphatic or aromatic hydrocarbon, in a glycol, or from another polymer matrix. Currently the diffusion is carried out at a temperature of 50–200° C. for a duration of 15 minutes to several hours, depending on the nature of the polymer matrix. Another implementation technique consists in mixing the photochrome in a formulation of polymerizable materials, in depositing this mixture on a surface or in a mold and in then carrying out the polymerization. These implementation techniques and others are described in the article by CRANO et al. "Spiroxazines and their use in photochromic lenses," published in Applied Photochromic Polymer Systems, Publishers Blackie and Son Ltd., 1992. According to a variant of the invention, it is also possible to consider grafting the photochromes onto (co) polymers. Thus, another aspect of the invention consists of the (co)polymers grafted with at least one of the photochromes described above.

As examples of preferred polymer materials for optical applications of the photochromic compound according to the invention, one can mention the following products: alkyl, cycloalkyl, aryl or arylalkyl poly(mono-, di-, tri-, tetra) acrylate or poly(mono-, di-, tri-, tetra) methacrylate, optionally halogenated or comprising at least ether and/or ester and/or carbonate and/or carbamate and/or thiocarbamate and/or urea and/or amide group; polystyrene, polycarbonate (e.g., bisphenol A polycarbonate, poly(carbonate of diallyl diethylene glycol), polyepoxy, polyurethane, polythiourethane, polysiloxane, polyacrylonitrile, polyamide, aliphatic or aromatic polyester, vinyl polymers, cellulose acetate, cellulose triacetate, cellulose acetatepropionate or polyvinylbutyral, copolymers of two or more types of monomers or mixtures of the above-mentioned polymers, preferably polycarbonate-polyurethane, poly (meth)acrylate-polyurethane, polystyrene-poly(meth) acrylate or polystyrene-polyacrylonitrile, advantageously a mixture of polyester and/or polycarbonate or poly(meth) acrylate.

The quantity of photochrome used in various articles depends on the desired degree of darkening. In particular, it is used in a quantity of 0.001–20 wt % of the total weight of the layer in which the photochrome is included. The photochromic compounds according to the invention can be used alone or in a mixture with other products to form a composition that can be in solid or liquid form, for example, in a solution or in a dispersion, as has already been mentioned above. These compositions, which constitute another object of the invention, can comprise one or more compounds (I) according to the invention and other complementary photochromic compounds which allow the attaining of dark colorations, for example, gray or brown, which the public desires in applications such as ophthalmic or sun-protection eyewear. These additional photochromic compounds can be those known to a person skilled in the art and described in the literature, for example, other naphthopyrans, benzopyrans, chromenes (U.S. Pat. Nos. 3,567,605, 5,238,981, World Patent No. 9,422,850, European Patent No. 562,915), spiropyrans or naphthospiropyrans (U.S. Pat. No. 5,238,981) and spiroxazines (CRANO et al., "Applied Photochromic Polymer Systems," Publishers Blackie & Son Ltd., 1992, Chapter 2).

These compositions according to the invention can also comprise:

Non-photochromic dyes allowing the adjustment of the tint, and/or one or more stabilizers, such as, for example, an antioxidant, and/or one or more anti-UV screens, and/or one or more anti[free]radical agents, and/or deactivators that deactivate the states of photochemical excitation.

These additives can enable further improvements in the durability of said compositions.

According to another one of its aspects pertaining to the application of the photochromic compounds (I), the present invention also relates to ophthalmic articles, such as articles of ophthalmic or sun protection eyewear articles, or eye shields comprising at least one compound according to the invention and/or at least one (co)polymer formed, at least in part, of repeating units derived from compounds having formula (I) and/or at least one composition comprising compounds (I) according to the invention, as defined above, and/or at least one matrix, as defined above, made of an organic polymer material or a mineral material or a mineral-organic hybrid material incorporating at least one compound of the invention.

In practice, the articles to which the present invention applies more particularly are photochromic ophthalmic or sun-protection lenses, glass paneling (glasses for buildings, for locomotion devices, automobiles), optical devices, decorative articles, sun-protection articles, information storage, etc.

The present invention will be better understood in the light of the following examples of synthesis and photochromic validation of compounds having the general formula (I). These examples are not intended to be interpreted as limiting the invention, but rather, show specific aspects of the invention within the broad generic scope disclosed.

EXAMPLES

Synthesis and Properties of Compounds in Table I, and Comparison to a Prior Art Compound C Example 1

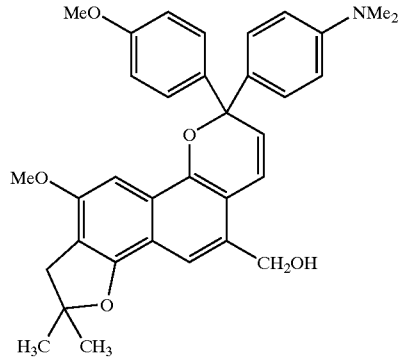

Step 1: 2,2-Dimethyl-2,3-dihydro-4-methoxy-benzofuran-7-carbaldehyde is synthesized from m-methoxyphenol, 3-chloro-2-methyl-propene according to the method described by Bradbury, et al., *J. Heterocyclic Chem.*, 26, 1827 (1989).

Step 2: The aldehyde from Step 1 (8.1 g), dimethyl succinate (10.3 g), and potassium t-butoxide (5.3 g) are mixed in 150 ml of toluene. The mixture is refluxed for 1.5 hours under nitrogen blanket. After it is cooled to room temperature, 200 ml of water is added and mixed well. The aqueous phase is separated, acidified with 5N HCl, and extracted with 3×100 ml of ethyl acetate. The combined extracts are washed once with water, dried over magnesium sulfate. The solvent is remove under reduced pressure to give 9.3 g of dark brown crude half-ester product (4-(2,2-dimethyl-2,3-dihydrobenzofuran-5-yl)-3-methoxycarbonyl-3-butenoic acid). It is used without purification.

Step 3: The crude half-ester from Step 2 is added to reaction flask containing 50 ml of acetic anhydride and 5.7 g of anhydrous potassium acetate. The mixture is refluxed for 2.5 hours, cooled, filtered. The solid in the filtration funnel is washed thoroughly with ethyl acetate. The combined filtrate is concentrated to just dry under vacuum. The dark solid is re-dissolved in ethyl acetate and washed with water, dried over magnesium sulfate. After removing the solvent, 8.7 g of crude cyclized product (2,2-dimethyl-2,3-dihydro-6-acetoxy-7-methoxycarbonyl-naphtho[1,2-b]furan) is obtained. It is used directly in the next step.

Step 4: The crude material from Step 3 is dissolved in 75 ml of methanol under reflux. One ml of concentrated HCl is added. The reaction solution is refluxed for 1.5 hours, cooled, concentrated. The product is separated by chromatography on a silica column using ethyl acetate/hexane (1:3) as eluent. An NMR shows that the product, 1.8 g of light yellow solid, has a structure of (2,2-dimethyl-2,3-dihydro-7-methoxycarbonyl-naphtho[1,2-b]furan-6-ol).

Step 5: The naphthol from the previous step (0.1 g) was reacted with 0.14 g of 1-(4-methoxyphenyl)-1-(4-N,N-dimethylaminophenyl)-2-propyn-1-ol in 5 ml of toluene in presence of catalytic amount of chloroacetic acid under reflux for 24 hours. The reaction solution was cooled, concentrated. A flash silica column with ethyl acetate/hexane 1:4 as eluent provided crude product as greenish viscose oil. It was used in the next step without reunification.

Step 6: The above crude product (0.1 g) was dissolved in 20 ml of toluene. The solution was cooled down to 0° C. Then, diisobutylaluminum hydride (0.5 ml, 1M in toluene) was added. The solution was stirred for 30 minutes at 0° C., quenched with water, warmed to room temperature, dried over magnesium sulfate. The whole mixture was then subjected to a silica column with ethyl acetate/hexane 1:4 as eluent. The photochromic portion was collected and dried to provide 0.03 g off-white powder. An NMR of the powder shows a structure of 2-(4-methoxyphenyl)-2-(4-N,N-dimethylaminophenyl)-5-methoxycarbonyl-9-methoxy-(5',5'-dimethyl-4',5'-dihydrofurano)[2',3':7,8]naphtho[1,2-b]pyran.

Example 2

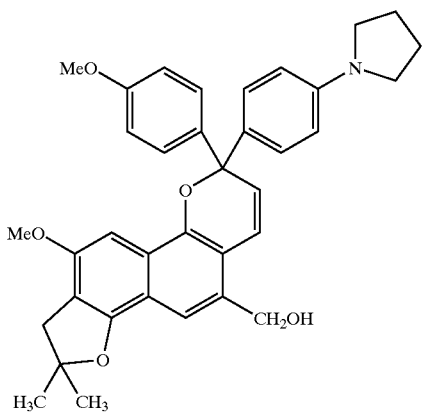

Step 1 to 4: The corresponding steps of Example 1 are followed to have 2,2-dimethyl-2,3-dihydro-4-methoxy-8-methoxycarbonyl-naphtho[1,2-b]furan-6-ol.

Step 5: The naphthol from the previous step (1.0 g) was reacted with 1.9 g of 1-(4-methoxyphenyl)-1-(4-pyrrolidinophenyl)-2-propyn-1-ol in 5 ml of toluene in presence of catalytic amount of chloroacetic acid under reflux for 24 hours. The reaction solution was cooled, concentrated. A flash silica column with ethyl acetate/hexane 1:4 as eluent provided 0.85 g crude product as greenish powder. It was used in the next step without purification.

Step 6: The above crude product (0.84 g) was dissolved in 200 ml of toluene. The solution was cooled down to 0° C. Then, diisobutylaluminum hydride (3 ml, 1M in toluene) was added. The solution was stirred for 30 minutes at 0° C., quenched with water, warmed to room temperature, dried over magnesium sulfate. The whole mixture was concentrated and then subjected to a silica column with ethyl acetate/hexane 1:4 as eluent. The photochromic portion was collected and dried to provide 0.56 g off-white powder. An NMR of the powder shows a structure of 2-(4-methoxyphenyl)-2-(4-pyrrolidinophenyl)-5-hydroxymethyl-9-methoxy-(5',5'-dimethyl-4',5'-dihydrofurano)[2',3':7,8]naphtho[1,2-b]pyran.

Example 3

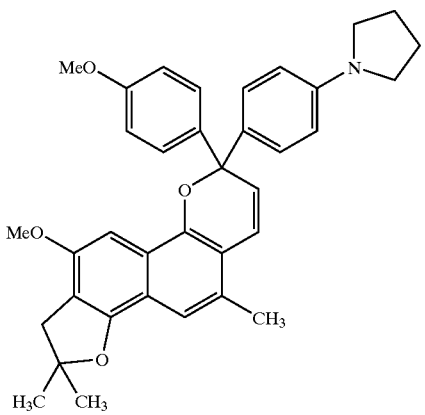

Step 1 to 4: The corresponding steps of Example 1 are followed to have 4-methoxy-8-methoxycarbonyl-2,2-dimethyl-2,3-dihydro-naphtho[1,2-b]furan-6-ol.

Step 5: The naphthofuran-ol (0.8 g) from the last step and imidazole (1.0 g) are dissolved in 15 ml of DMF. To this solution is then added 10 ml of t-butyldimethylsilyl chloride (1M in THF). The reaction solution is stirred overnight at room temperature, quenched with few milliliters of water, diluted with 100 ml of ether, then washed with water thoroughly. The organic phase is separated, dried over magnesium sulfate. After removing the solvent, a light yellow crystal product, 1.2 g, is obtained. It is pure enough for the next step.

Step 6: The above protected naphthofuran-ol (1.1 g) is dissolved in 15 ml of anhydrous toluene. Diisobutylaluminum hydride (5.5 ml, 1M in toluene) is transfer into the solution at a rate that the reaction temperature is not over 40° C. After an additional 30 minutes of stirring at room temperature, the reaction is quenched with 0.5 ml of water, diluted with 30 ml of ether, dried with magnesium sulfate, and then filtered. The gel solid in the filtration funnel is washed with ether twice. The combined organic liquid phase is then dried under reduced pressure to obtain a solid product, 1.0 g, which is pure enough for the next step. An NMR spectrum shows the product has a structure of 2,2-dimethyl-2,3-dihydro-4-methoxy-6-t-butyldimethylsiloxy-8-hydroxymethyl-naphtho[1,2-b]furan.

Step 7: To a suspension of pyridinium chlorchromate (7.0 g, 20 wt % on basic alumina) in 15 ml of dichloromethane is added 1.0 g of the naphthalene from the previous step. After stirring for 2 hours (or until TLC shows the reaction is complete), the solid is filtered, washed with three 20 ml portions of ether. The combined filtrates are evaporated to give 0.7 g of 2,2-dimethyl-2,3-dihydro-4-methoxy-6-t-butyldimethylsiloxy-naphtho[1,2-b]furan-8-carbaldehyde. An NMR spectrum confirms the structure.

Step 8: A mixture of the above naphthaldehyde (0.92 g), hydrazine hydride (0.6 ml, N$_2$H$_4$ 55%), potassium hydroxide (0.6 g), and diethylene glycol (10 ml) is refluxed for 2 hours. The condenser is then put downward, and the reaction temperature is gradually increased to around 195° C. After 4 hours at this temperature, the system is cooled, 15 ml of water is added, organic is extracted with two 30 ml portions of toluene. The combined toluene extracts are washed with water once, dried with magnesium sulfate, evaporated with a rotary evaporator. The residual is subjected to a silica column with ethyl acetate/hexane 1:4 as eluent. An NMR spectrum indicates that the recovered product, 0.29 g, has a structure of 4-methoxy-8-methyl-2,2-dimethyl-2,3-dihydro-naphtho[1,2-b]furan-6-ol.

Step 9: A mixture of the naphthofuran-ol (0.28 g) from Step 8, 1-(4-methoxyphenyl)-1-(4-pyrrolidinophenyl)-2-propyn-1-ol (0.50 g), and catalytic amount of chloroacetic acid in 10 ml of is refluxed for 3 hours. The reaction solution is cooled, concentrated. The product, 0.10 g of cream powder, is obtained by silica column separation with ethyl acetate/hexane 1:4 as eluent. An NMR confirms the structure to be 2-(4-methoxyphenyl)-2-(4-pyrrolidinophenyl)-5-methyl-9-methoxy-(5',5'-dimethyl-4',5'-dihydrofurano)[2',3':7,8]naphtho[1,2-b]pyran.

Example 4

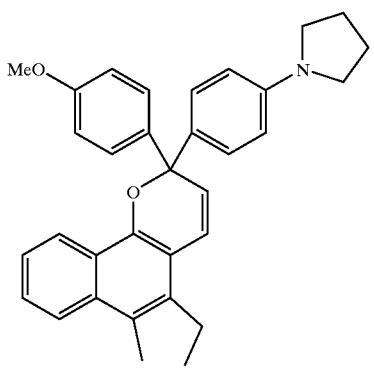

Step 1:2-Methyl-2,3-dihydronaphtho[1,2-b]furan-5-ol is synthesized from 1-naphthol and allyl chloride according to the route described in Cameron et al., *Aust. J. Chem.*, 1983, 35, p1481.

Step 2: A mixture of the above naphthofuran-ol (3.0 g), 1-(4-methoxyphenyl)-1-(4-pyrrolidinophenyl)-2-propyn-1-ol (1.0 g), and catalytic amount of chloroacetic acid in 100 ml of is refluxed for 3 hours. The reaction solution is cooled, concentrated. After a silica column separation with ethyl acetate/hexanes 1:4 as eluent, 0.4 g of photochromic violet oil is obtained.

Example 5

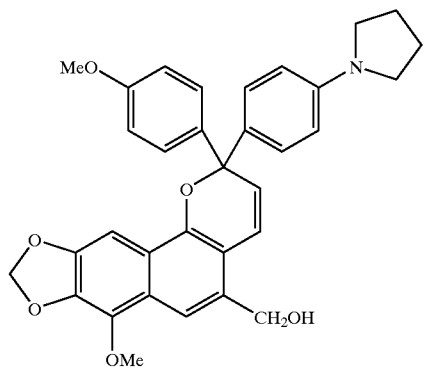

Step 1: A mixture of 3-methoxycatechol (10 g), diiodomethane (23 g), and anhydrous potassium carbonate (20 g) in 35 ml DMF is heated up to 100° C. and stirred at this temperature for 2 to 3 hours, then cooled, diluted with water, extracted with three portions of ether. The ether extracts are combined, washed with water once, dried over magnesium sulfate, evaporated. The residual is purified by a flash column chromatography on silica gel with ethyl acetate/hexane 1:4 as eluent to give colorless liquid product, 6.7 g. The structure is confirmed by a NMR spectrum to be 3-methoxy-1,2-methylenedioxybenzene.

Step 2: Phosphorus oxychloride (7.5 ml) is added dropwise to a stirred solution of 3-methoxy-1,2-methylenedioxybenzene (4.9 g) in anhydrous dimethylformamide (30 ml). The reaction mixture is heated in a water bath for 4 hours. It is then cooled and poured over ice/water (300 ml). Saturated sodium carbonate solution is used to adjust the pH of the mixture to just basic. The mixture is extracted with ether (2×100). The combined ether extracts is washed with water, dried over magnesium sulfate. After removing the solvent under reduced pressure, the residual is subjected to a flash silica column, which provides 2.6 g of white crystal product, and recovered 1.7 g of starting material. NMR shows that the product has a structure of (1-methoxy-2,3-methylenedioxybenzaldehyde). It is used directly in the next step.

Steps 3 to 6: Steps 2 to 5 of Example 1 are followed except that 1-methoxy-2,3-methylenedioxybenzaldehyde is used in place of 2,3-dihydrobenzofuran-7-carbaldehyde.

Step 7: The photochromic product, 2-(4-methoxyphenyl)-2-(4-pyrrolidinophenyl)-5-methoxycarbonyl-7-methoxy-8,9-methylenedioxy-naphtho[1,2-b]pyran obtained in last step (0.35 g) is dissolved in 85 ml of toluene. The solution is cooled down to 0° C. Then, 1.7 ml of diisobutylaluminum hydride (1M in toluene) is added. The solution is stirred for 30 minutes at 0° C., quenched with 0.2 ml of water, warmed to room temperature, dried over magnesium sulfate, and filtered. The gel solid in the filtration funnel is washed with ethyl acetate twice. The combined organic liquid phase is then dried under reduced pressure. The desired product, 0.08 g of off-white solid (while 0.2 g of starting material is recovered), is crystallized with ethyl acetate/hexane. The structure is confirmed by an NMR spectrum to be 2-(4-methoxyphenyl)-2-(4-pyrrolidinophenyl)-5-hydroxymethyl-7-methoxy-8,9-methylenedioxy-naphtho[1,2-b]pyran.

Example 6

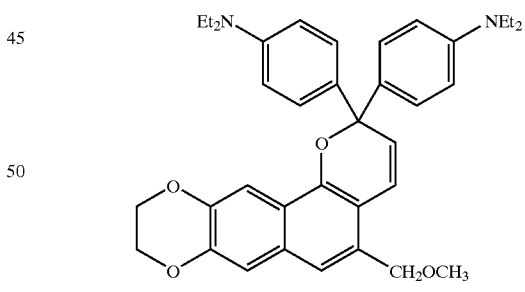

Steps 1 to 3: Steps 2 to 4 of Example 1 are followed except that 1,4-benzodioxan-6-carboxaldehyde is used in place of 2,3-dihydrobenzofuran-7-carbaldehyde to obtain 8-methoxycarbonyl-1,4-naphtho[2,3-b]dioxane-6-ol.

Step 4: To a solution of the above naphthodioxane-6-ol (1.85 g) in 100 ml of toluene is added 7.1 ml of diisobutylaluminum hydride (1M in toluene) at room temperature. The solution is stirred for 30 minutes, quenched with 6 ml of water, dried over magnesium sulfate, and filtered. The gel solid in the filtration funnel is washed with ethyl acetate twice. The combined organic liquid phase is then dried under reduced pressure. The desired product, 1.35 g of off-white solid, is obtained after crystallization with ethyl acetate/hexane. The structure is confirmed by an NMR spectrum to be 8-hydroxymethyl-1,4-naphtho[2,3-b]dioxane-6-ol.

Step 5: To a solution of 1.35 g of 8-hydroxymethyl-1,4-naphtho[2,3-b]dioxane-6-ol in 150 ml of methanol was added 0.55 g of p-toluenesulfonic acid. After refluxing for 6 hours and stirring at room temperature overnight, the solution was neutralized with 5.8 ml of 0.5N NaOH. It was then concentrated. 100 ml of each ethyl acetate and water were added, washed, and the organic phase was separated, dried over magnesium sulfate, filtered, and concentrated again. A final flash silica column yielded 0.93 g tan product. Its structure was confirmed by NMR to be 8-methoxymethyl-1,4-naphtho[2,3-b]dioxane-6-ol.

Step 6: A mixture of the above naphthol (0.43 g), 1,1-di(4-N,N-diethylaminophenyl)-2-propyn-1-ol (1.00 g), and catalytic amount of chloroacetic acid in 25 ml of is refluxed for 3 hours. The reaction solution is cooled, concentrated. After a silica column separation, a photochromic bluish white powder, 0.20 g, is obtained. Its structure, 2,2-di(4-N,N-diethylaminophenyl)-5-methoxymethyl-8,9-ethylenedioxy-naphtho[1,2-b]pyran, is confirmed by an NMR spectrum.

Comparison Compound C

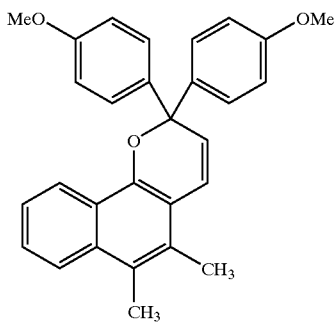

This compound is available commercially.

Photochromic Property Measurement:

Each of the compounds is dissolved in chloroform at a concentration of 0.1%. The UV-visible absorptions (optical path of 1 cm) are then measured before and after exposure to a 365 nm UV source. The tints and intensities developed under the sun are also recorded. The photochromic properties: λmax of the two principle absorption bands, bleach rate ($t^{1/2}$), and color/intensity, of these compounds are given in the Table I below.

TABLE I

| Compound | $\lambda_1$ (nm) | $\lambda_2$ (nm) | $t_{1/2}$ bleaching (seconds) | Color/Intensity |
|---|---|---|---|---|
| 1 | 480 | 578 | 43 | blue/high |
| 2 | 485 | 592 | 30 | blue/high |
| 3 | 490 | 588 | 59 | blue/high |
| 4* | — | 570 | 550 | violet/medium |
| 5 | 480 | 575 | 29 | violet-blue/high |
| 6 | 480 | 592 | 17 | blue/medium |
| C | 430 | 510 | 45 | red/medium |

*Measured in acetone

It is demonstrated by these measurements that the naphthopyrans of the invention have higher $\lambda_{max}$ values for both primary and secondary absorption bands, and most of them display much higher intensity compared to the prior art compound C, which does not have an oxygen-heterocyclic ring fused to the naphthalene ring. In addition, it has been observed that there also exist a bathochromic shift of approximately 8 nm for the UV $\lambda_{max}$ of the compounds according to the invention in comparison to compound C. This shift consequently allows a better sensitivity to the UV portion of the solar radiation spectrum. Articles embodying this invention should comprise a polymer binder and should contain an amount of naphthopyran that is sufficient to enable visual observation of a photochromic effect in a layer comprising the polymeric binder. This is referred to as a photochromic amount.

What is claimed is:

1. A photochromic article comprising a layer of polymeric binder containing a naphthopyran having a central nucleus of the formula:

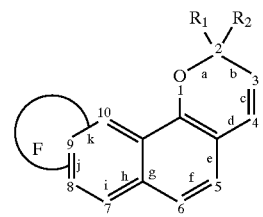

wherein F is an oxygen-containing 5- to 7-member heterocyclic ring group, its 2,3 or 3,2 positions fused to the f, i, j, or k side of the ring, and $R_1$ and $R_2$ are the atoms or groups providing photochromic properties to the naphthopyran.

2. A photochromic article according to claim 1 wherein $R_1$ and $R_2$ are selected from the group consisting of a hydrogen, a linear or branched alkyl group of 1 to 12 carbon atoms, a cycloalkyl group of 3 to 12 carbon atoms, an aryl group of 6 to 24 ring carbon atoms or b) a heteroaryl group of 4 to 24 carbon atoms respectively and at least one hetero ring atom selected from sulfur, oxygen and nitrogen; and wherein $R_1$ and $R_2$ together form an adamantyl, norbornyl, fluorenylidene, di(C1–C6)alkylanthracenylidene or spiro (C5–C6)cycloalkylanthracenylidene group.

3. A photochromic article comprising a layer of polymeric binder containing a naphthopyran having the central nucleus of:

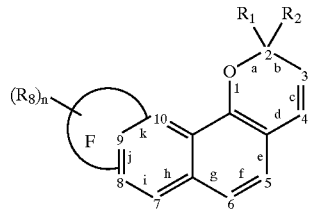

wherein F is an oxygen-containing 5- to 7-member heterocyclic ring group, its 2,3 or 3,2 positions fused to the f, i, j, or k side of the ring group, $R_1$ and $R_2$ are the atoms or groups providing photochromic properties to the naphthopyran; and each $R_8$ group can be the same or different, independently representing
 a hydrogen,
 a halogen,
 a linear or branched alkyl group which comprises 1 to 12 carbon atoms, a cycloalkyl group comprising 3 to 12 carbon atoms, and two of the $R_8$ groups, which are adjacent or bonded to the same carbon atom in the group F, form a 5- to 6-membered non-aromatic ring which may comprise at least one heteroatom selected from the group consisting of oxygen, sulfur, and nitrogen.

4. A photochromic article comprising a layer of polymeric binder containing a naphthopyran having a central nucleus of the formula:

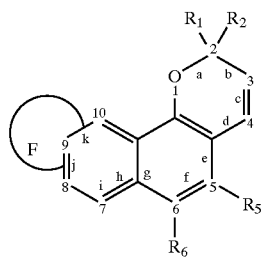

wherein F is an oxygen-containing 5- to 7-member heterocyclic ring group, its 2,3 or 3,2 positions fused to the f, i, j, or k side of the ring, and $R_1$ and $R_2$ are the atoms or groups necessary to provide photochromic properties to the naphthopyran and $R_5$ and $R_6$ are selected from the group consisting of:
a hydrogen,
a halogen,
a linear or branched alkyl group of 1 to 12 carbon atoms,
a cycloalkyl group of 3 to 12 carbon atoms,
a linear or branched alkoxy group of 1 to 12 carbon atoms;,
a haloalkyl, halocycloalkyl, or haloalkoxy group,
a linear or branched alkenyl or alkynyl group of 1–12 carbon atoms,
a linear or branched alkenyloxy or alkynyloxy group of 1–12 carbon atoms,
an aryl or heteroaryl group,
an aralkyl or heteroaralkyl group, the alkyl group, which is linear or branched, of 1 to 4 carbon atoms;
an amine or amide group: $-NH_2$, $-NHR_{11}$, $-CONH_2$, $-CONHR_{11}$,

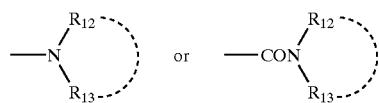

$R_{11}$ representing a linear or branched alkyl group of 1 to 6 carbon atoms, $R_{12}$ and $R_{13}$ which are the same or different, independently representing a linear or branched alkyl group of 1 to 6 carbon atoms, or representing together with the nitrogen atom to which they are bound a 5- to 7-membered ring which comprise at least one other heteroatom selected from oxygen, sulfur and nitrogen;

a $-C(R_{16})_2X$ group, wherein X is selected from the group consisting of
$-CN$, halogen, hydroxy, alkoxy, benzoyloxy, C1–C6 acyloxy, amino, C1–C6 mono-alklamino, C1–C6 dialkyl amino, morpholino, piperidino, 1-indolinyl, pyrrolidyl, or trimethylsilyloxy, $R_{16}$ is hydrogen, C1–C6 alkyl, phenyl or naphthyl with C1–C6 alkyl or C1–C6 alkoxy substituents, an $-OCOR_{17}$ or $-COOR_{17}$ group, $R_{17}$ representing a straight or branched alkyl group comprising 1 to 6 carbon atoms, or a cycloalkyl group comprising 3 to 6 carbon atoms, or a phenyl group,
a methacryloyl group or an acryloyl group, an epoxy group,
a polyether, polyamide, polycarbonate, polycarbamate, polyurea or polyester residue;
an aralkyl or heteroaralkyl group, the alkyl group, which is linear or branched, comprising 1 to 4 carbon atoms,
$R_5$ and $R_6$ together form a 5- to 7-member aromatic or non-aromatic ring, the ring may comprising at least one heteroatom selected from oxygen, sulfur, and nitrogen.

5. The photochromic article according to claim 1 comprising a polymeric organic host material and a photochromic amount of the naphthopyran compound.

6. The photochromic article of claim 5 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

7. The photochromic article of claim 5 wherein the polymeric organic host material is a solid transparent polymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

8. The photochromic article of claim 6 wherein the photochromic compound is present in an amount of from 0.05 to 1.0 milligram per square centimeter of organic host material surface to which the photochromic substance(s) is incorporated or applied.

9. The photochromic article of claim 8 wherein said transparent polymer is an optical element.

10. The photochromic article of claim 9 wherein said optical element is a lens.

11. The photochromic article of claim 1 comprising a polymeric organic host material and a photochromic amount of the naphthopyran compound.

12. The photochromic article of claim 11 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

13. The photochromic article of claim 11 wherein the polymeric organic host material is a solid transparent polymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

14. The photochromic article of claim 13 wherein the photochromic compound is present in an amount of from 0.05 to 1.0 milligram per square centimeter of organic host material surface to which the photochromic substance(s) is incorporated or applied.

15. The photochromic article of claim 14 wherein said transparent polymer is an optical element.

16. The photochromic article of claim 14 wherein said optical element is a lens.

17. The photochromic article of claim 16 wherein the refractive index of the polymerizate is from about 1.48 to about 1.75.

18. The photochromic article of claim 1 wherein the naphthopyran is represented by the general formula:

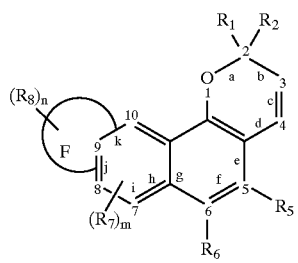

(I)

wherein the ring group F comprises 5 ring atoms consisting of C and O, and F is fused to the f side, m is an integer from 0 to 2 and n is an integer from 0 to 4.

19. The photochromic article of claim 1 wherein the naphthopyran is represented by the general formula:

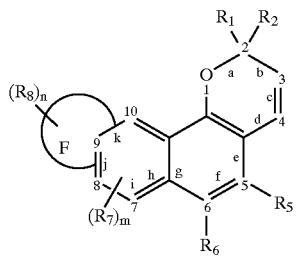

(I)

wherein the ring group F comprises 5 ring atoms consisting of C and O, and F is fused to the i side, m is an integer from 0 to 2 and n is an integer from 0 to 4.

20. The photochromic article of claim 1 wherein the naphthopyran is represented by the general formula:

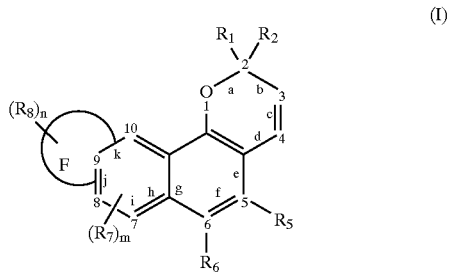

(I)

wherein the ring group F comprises 5 ring atoms consisting of C and O, and F is fused to the j side, m is an integer from 0 to 2 and n is an integer from 0 to 4.

21. The photochromic article of claim 1 wherein the naphthopyran is represented by the general formula:

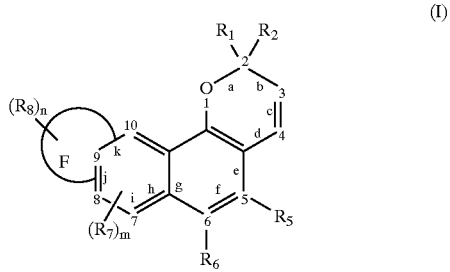

(I)

wherein the ring group F comprises 5 ring atoms consisting of C and O, and F is fused to the k side, m is an integer from 0 to 2 and n is an integer from 0 to 4.

22. The photochromic article of claim 1 wherein the naphthopyran is represented by the general formula:

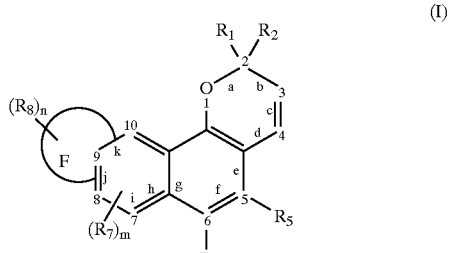

(I)

wherein the ring group F comprises 6 ring atoms consisting of C and O, and F is fused to the f side, m is an integer from 0 to 2 and n is an integer from 0 to 4.

23. The photochromic article of claim 1 wherein the naphthopyran is represented by the general formula:

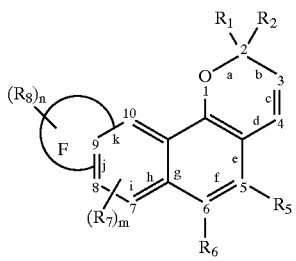

(I)

wherein the ring group F comprises 6 ring atoms consisting of C and O, and F is fused to the i side, m is an integer from 0 to 2 and n is an integer from 0 to 4.

24. The photochromic article of claim 1 wherein the naphthopyran is represented by the general formula:

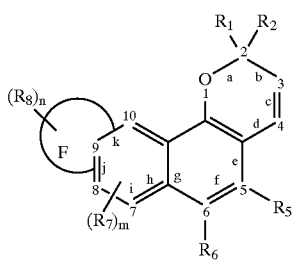

(I)

wherein the ring group F comprises 6 ring atoms consisting of C and O, and F is fused to the j side, m is an integer from 0 to 2 and n is an integer from 0 to 4.

25. The photochromic article of claim 1 wherein the naphthopyran is represented by the general formula:

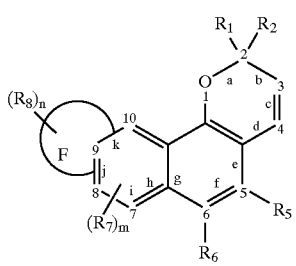

(I)

wherein the ring group F comprises 6 ring atoms consisting of C and O, and F is fused to the k side, m is an integer from 0 to 2 and n is an integer from 0 to 4.

26. A photochromic article according to claim 4 wherein $R_5$ and $R_6$ are the same or different and they represent, independently:
 a hydrogen,
 a halogen,
 a linear or branched alkyl group of 1 to 12 carbon atoms,
 a cycloalkyl group of 3 to 12 carbon atoms,
 a linear or branched alkoxy group of 1 to 12 carbon atoms,
 a haloalkyl, halocycloalkyl, or haloalkoxy group,
 a linear or branched alkenyl or alkynyl group of 1–12 carbon atoms,
 a linear or branched alkenyloxy or alkynyloxy group of 1–12 carbon atoms,
 an aryl or heteroaryl group, and
 an aralkyl or heteroaralkyl group, the alkyl group being of 1 to 4 carbon atoms.

27. A photochromic article comprising a polymeric binder and a naphthopyran of the formula (I):

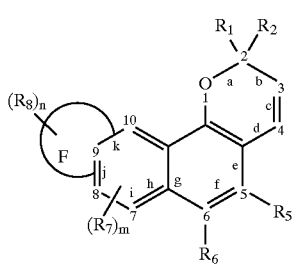

(I)

in which:
 F is an oxygen-containing 5- to 7-member heterocyclic ring with or without substitutions, its 2,3 or 3,2 positions fused to the f, i, j, or k side of the ring,
 $R_1$ and $R_2$ independently represent:
  a hydrogen,
  a linear or branched alkyl group which comprises 1 to 12 carbon atoms,
  a cycloalkyl group which comprises 3 to 12 carbon atoms,
  an aryl or heteroaryl group which comprises in its basic structure (that is, in its ring atoms, the rings comprising 5, 6 or 7 atoms) 6 to 24 carbon atoms or 4 to 24 carbon atoms respectively and at least one heteroatom selected from sulfur, oxygen and nitrogen; the basic structure being optionally substituted with at least one substituent selected from:
   a halogen atom,
   a hydroxy group,
   a linear or branched alkyl group comprising 1 to 12 carbon atoms,
   a linear or branched alkoxy group comprising 1 to 12 carbon atoms,
   a haloalkyl or haloalkoxy group corresponding to the ($C_1$–$C_{12}$) alkyl or alkoxy groups above respectively which are substituted with at least one halogen atom,
   a linear or branched alkenyl group comprising 2 to 12 carbon atoms,
   an —$NHR_{11}$ group, $R_{11}$ representing a linear or branched alkyl group comprising 1 to 6 carbon atoms,
   a

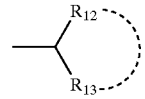

group, in which $R_{12}$ and $R_{13}$, which are the same or different, independently representing a linear or branched alkyl group comprising 1 to 6 carbon atoms, or representing, together with the nitrogen atom to which they are bound, a 5- to 7-membered ring which can comprise at least one other heteroatom selected from oxygen, sulfur and nitrogen, said nitrogen being optionally substituted with an $R_{14}$ group, which is a linear or branched alkyl group comprising 1 to 6 carbon atoms, a methacryloyl group or an acryloyl group, an aralkyl or heteroaralkyl group, the alkyl group, which is linear or branched, comprising 1 to 4 carbon atoms and the aryl and heteroaryl groups having the definitions given above, or the two substituents $R_1$ and $R_2$ together forming ring group selected from the group consisting of adamantyl, norbornyl, fluorenylidene, 5,5- or 10,10-di(C1–C6) alkylanthracenylidene, 5 (or 10)-(C1–C6)alkyl-5 (or 10)-OH (or $OR_{15}$)anthracenylidene or spiro(C5–C6) cycloalkylanthracenylidene ring group; said ring group being optionally substituted with at least one of the substituents listed above in the definitions for $R_1$, $R_2$; said ring group being optionally substituted with two adjacent groups that form a 5- to 6-member aromatic or non-aromatic ring which can comprise at least one heteroatom selected from oxygen, sulfur, and nitrogen;

$R_5$ and $R_6$ are the same or different and they represent, independently:

a hydrogen, a halogen, and notably fluorine, chlorine or bromine, a linear or branched alkyl group which comprises 1 to 12 carbon atoms, a cycloalkyl group comprising 3 to 12 carbon atoms, a linear or branched alkoxy group comprising 1 to 12 carbon atoms, a haloalkyl, halocycloalkyl, or haloalkoxy group corresponding to the alkyl, cycloalkyl, alkoxy groups above respectively, which are substituted with at least one halogen atom, selected from the group consisting of fluorine, chlorine and bromine, a linear or branched alkenyl or alkynyl group comprising 1–12 carbon atoms, a linear or branched alkenyloxy or alkynyloxy group comprising 1–12 carbon atoms, an aryl or heteroaryl group having the same definition as that given above for aryl or heteroaryl groups within the definitions of $R_1$, $R_2$, an aralkyl or heteroaralkyl group, the alkyl group, which is linear or branched, comprising 1 to 4 carbon atoms, and the aryl and heteroaryl groups having the same definitions as those given above for $R_1$, $R_2$,

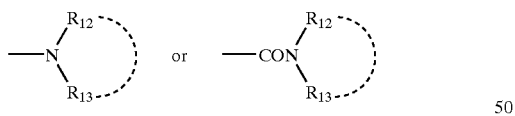

an amine or amide group: —$NH_2$, —$NHR_{11}$, —$CONH_2$, —$CNHR_{11}$, $R_{11}$, $R_{12}$, and $R_{13}$ having their respective definitions given above for the amine substituents of the values $R_1$, $R_2$, a —$C(R_{16})_2X$ group, wherein X is —CN, halogen, hydroxy, alkoxy, benzoyloxy, C1–C6 acyloxy, amino, C1–C6 mono-alklamino, C1–C6 dialkyl amino, morpholino, piperidino, 1-indolinyl, pyrrolidyl, or trimethylsilyloxy, $R_{16}$ is hydrogen, C1–C6 alkyl, phenyl or naphthyl with C1–C6 alkyl or C1–C6 alkoxy substituents, an —$OCOR_{17}$ or —$COOR_{17}$ group, $R_{17}$ representing a straight or branched alkyl group comprising 1 to 6 carbon atoms, or a cycloalkyl group comprising 3 to 6 carbon atoms, or a phenyl group, optionally substituted with at least one of the substituents listed above within the values in the definitions of $R_1$, $R_2$, a methacryloyl group or an acryloyl group, or an epoxy group having the formula,

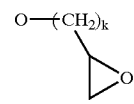

in which k=1, 2 or 3, $R_5$ and $R_6$ together form a 5- to 7-member aromatic or non-aromatic ring which can comprise at least one heteroatom selected from oxygen, sulfur, and nitrogen, and/or at least one substituent selected from the group consisting of a C1 to C6 alkyl group which is linear or

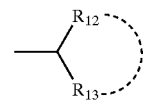

branched, a C1 to C6 alkoxy group which is linear or branched, and an amine group of formula —$NH_2$, $NHR_{11}$, or as defined in $R_1$ and $R_2$ for amine groups, a polyether, polyamide, polycarbonate, polycarbamate, polyurea or polyester residue;

each $R_7$ group can be same or different, independently representing a hydrogen, a halogen selected from the group consisting of fluorine, chlorine or bromine, a linear or branched alkyl group which comprises 1 to 12 carbon atoms, a cycloalkyl group comprising 3 to 12 carbon atoms, a linear or branched alkoxy group comprising 1 to 12 carbon atoms, a haloalkyl, halocycloalkyl, or haloalkoxy group corresponding to the alkyl, cycloalkyl, alkoxy groups described above respectively, which are substituted with at least one halogen atom selected from the group consisting of fluorine, chlorine and bromine, a linear or branched alkenyl or alkynyl group comprising 1–12 carbon atoms, a linear or branched alkenyloxy or alkynyloxy group comprising 1–12 carbon atoms, an aryl or heteroaryl group having the same definition as that given supra for $R_1$, $R_2$, an aralkyl or heteroaralkyl group, the alkyl group, which is linear or branched, comprising 1 to 4 carbon atoms, and the aryl and heteroaryl groups having the same definitions as those given above for $R_1$, $R_2$, an amine or amide group, such as —$NH_2$, —$NHR^{11}$, —$CONH_2$, —$CONHR^{11}$,

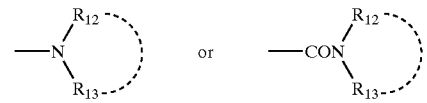

$R_9$, $R_{10}$, and $R_{12}$ having their respective definitions given above for the amine substituents and for the definitions of $R_1$, $R_2$, a —$C(R_{16})_2X$ group, wherein X is —CN, halogen, hydroxy, alkoxy, benzoyloxy, C1–C6 acyloxy, amino, C1–C6 mono-alklamino, C1–C6 dialkyl amino, morpholino, piperidino, 1-indolinyl, pyrrolidyl, or trimethylsilyloxy, $R_{16}$ is hydrogen, C1–C6 alkyl, phenyl or naphthyl with C1–C6 alkyl or C1–C6 alkoxy substituents, an —OCOR$_{17}$ or —COOR$_{17}$ group, $R_{17}$ representing a straight or branched alkyl group comprising 1 to 6 carbon atoms, or a cycloalkyl group comprising 3 to 6 carbon atoms, or a phenyl group, optionally substituted with at least one of the substituents listed above for the values of $R_1$, $R_2$:aryl or heteroaryl, a methacryloyl group or an acryloyl group, an epoxy group having the formula,

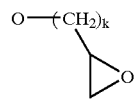

in which k 1, 2 or 3, a polyether, polyamide, polycarbonate, polycarbamate, polyurea or polyester residue, m is an integer from 0 to 2;

F may be substituted with one or more groups $R_8$ group, which may be the same or different, and independently represent a hydrogen, a halogen, and notably fluorine, chlorine or bromine, a linear or branched alkyl group which comprises 1 to 12 carbon atoms, a cycloalkyl group comprising 3 to 12 carbon atoms, and two of the $R_8$ groups, which are adjacent or bonded to the same carbon atom in the group F, form a 5- to 6-membered non-aromatic ring which can comprise at least one heteroatom selected from the group consisting of oxygen, sulfur, and nitrogen.

28. The photochromic article of claim 27 wherein $R_7$ and $R_9$ are methoxy groups.

29. The photochromic article of claim 27 in which $R_5$, $R_6$, $R_{10}$ are independently selected from the group consisting of hydrogen atoms or linear or branched or cyclic alkyl groups of 1 to 7 carbon atoms.

30. The photochromic article of claim 27 wherein the naphthopyran has a structure:

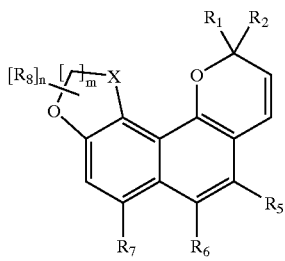

(Ia)

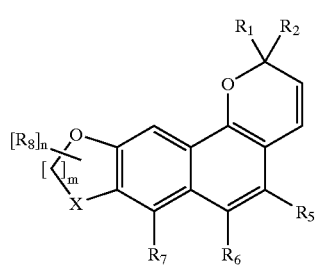

(Ib)

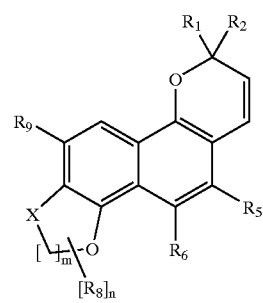

(Ic)

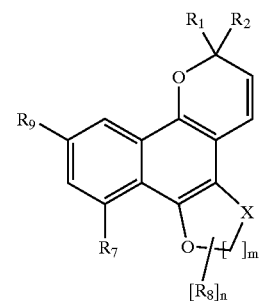

(Id)

where m is 1 or 2, X is a carbon or oxygen atom, $R_5$ is selected from groups of methyl, hydroxymethyl, and methoxymethyl, and at least one of $R_7$ and $R_9$ is alkoxy group.

31. A photochromic article comprising a polymeric binder and a naphthopyran having a central nucleus of the formula:

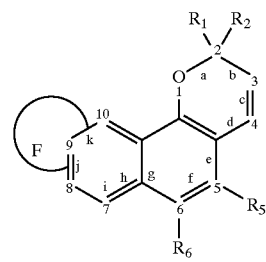

wherein F is an oxygen-containing 5- to 7-member heterocyclic ring group, its 2,3 or 3,2 positions fused to the f, i, j, or k side of the ring, and $R_1$ and $R_2$ are the atoms or groups necessary to provide photochromic properties to the naphthopyran and $R_5$ and $R_6$ are selected from the group consisting of:

a hydrogen, a halogen, a linear or branched alkyl group of 1 to 12 carbon atoms, a cycloalkyl group of 3 to 12 carbon atoms, a linear or branched alkoxy group of 1 to 12 carbon atoms, a linear or branched alkenyl or alkynyl group of 1–12 carbon atoms, a linear or branched alkenyloxy or alkynyloxy group of 1–12 carbon atoms, an aryl or heteroaryl group, and an aralkyl or heteroaralkyl group, the alkyl group, which is linear or branched, of 1 to 4 carbon atoms.

32. A photochromic article according to claim 1 wherein the naphthopyran has the formula (I):

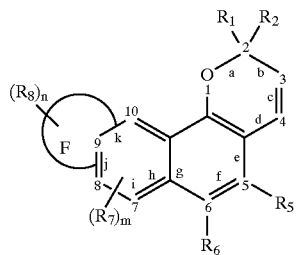

(I)

in which:
F is an oxygen-containing 5- to 7-member heterocyclic ring group, its 2,3 or 3,2 positions fused to the f, i, j, or k side of the ring,
$R_1$ and $R_2$ independently represent:
a hydrogen,
a linear or branched alkyl group of 1 to 12 carbon atoms,
a cycloalkyl group of 3 to 12 carbon atoms,
an aryl group of 6 to 24 ring carbon atoms or b) a heteroaryl group of 4 to 24 carbon atoms respectively and at least one heteroatom selected from sulfur, oxygen and nitrogen;
a methacryloyl group or an acryloyl group,
an aralkyl or heteroaralkyl group, the alkyl group, which is linear or branched, comprising 1 to 4 carbon atoms and the aryl and heteroaryl groups having the definitions given above, or
$R_1$ and $R_2$ may together form a ring group an adamantyl, norbornyl, fluorenylidene, di(C1–C6) alkylanthracenylidene or spiro(C5–C6) cycloalkylanthracenylidene group;
F may be substituted with one or more groups $R_8$ group, which may be the same or different, and independently represent
a hydrogen,
a halogen, and notably fluorine, chlorine or bromine,
a linear or branched alkyl group which comprises 1 to 12 carbon atoms,
a cycloalkyl group comprising 3 to 12 carbon atoms.

33. A photochromic article comprising a polymeric binder and a naphthopyran is represented by the general formula:

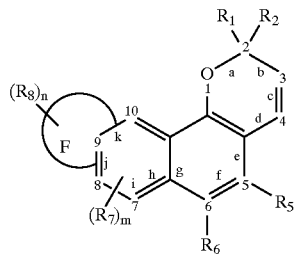

(I)

wherein wherein F is an oxygen-containing 5- to 7-member heterocyclic ring group, its 2,3 or 3,2 positions fused to the f, i, j, or k side of the ring, and
$R_1$ and $R_2$ are the atoms or groups providing photochromic properties to the naphthopyran, wherein the ring group F comprises 5 ring atoms consisting of C and O, and F is fused to the f side,
$R_5$ and $R_6$ are selected from the group consisting of:
a hydrogen,
a halogen,
a linear or branched alkyl group of 1 to 12 carbon atoms,
a cycloalkyl group of 3 to 12 carbon atoms,
a linear or branched alkoxy group of 1 to 12 carbon atoms,
a linear or branched alkenyl or alkynyl group of 1–12 carbon atoms,
a linear or branched alkenyloxy or alkynyloxy group of 1–12 carbon atoms,
an aryl or heteroaryl group, and
an aralkyl or heteroaralkyl group, the alkyl group, which is linear or branched, of 1 to 4 carbon atoms, and
m is an integer from 0 to 2 and n is an integer from 0 to 4.

34. A photochromic article comprising a polymeric binder and a naphthopyran represented by the general formula:

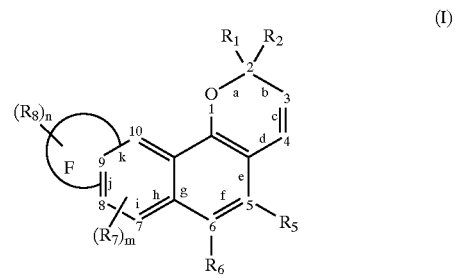

(I)

wherein F is an oxygen-containing 5- to 7-member heterocyclic ring group, its 2,3 or 3,2 positions fused to the f, i, j, or k side of the ring, and
$R_1$ and $R_2$ are the atoms or groups providing photochromic properties to the naphthopyran, and the ring group F comprises 5 ring atoms consisting of C and O, and F is fused to the i side,
$R_5$ and $R_6$ are selected from the group consisting of:
a hydrogen,
a halogen,
a linear or branched alkyl group of 1 to 12 carbon atoms,
a cycloalkyl group of 3 to 12 carbon atoms,
a linear or branched alkoxy group of 1 to 12 carbon atoms,
a linear or branched alkenyl or alkynyl group of 1–12 carbon atoms,
a linear or branched alkenyloxy or alkynyloxy group of 1–12 carbon atoms,
an aral or heteroaralkyl group, and
an aralkyl or heteroaralkyl group, the alkyl group, which is linear or branched, of 1 to 4 carbon atoms, and
m is an integer from 6 to 2 and n is an integer from 0 to 4.

35. A photochromic article comprising a polymeric binder and a naphthopyran represented by the general formula:

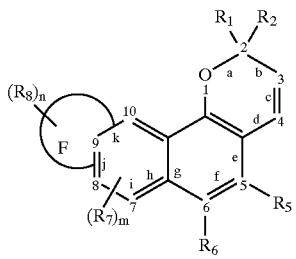

wherein $R_1$ and $R_2$ are the atoms or groups providing photochromic properties to the naphthopyran, and the ring group F comprises 5 ring atoms consisting of C and O and the ring group F comprises 5 ring atoms consisting of C and O, and F is fused to the j side, $R_5$ and $R_6$ are selected from the group consisting of:
 a hydrogen,
 a halogen,
 a linear or branched alkyl group of 1 to 12 carbon atoms,
 a cycloalkyl group of 3 to 12 carbon atoms,
 a linear or branched alkoxy group of 1 to 12 carbon atoms,
 a linear or branched alkenyl or alkynyl group of 1–12 carbon atoms,
 a linear or branched alkenyloxy or alkynyloxy group of 1–12 carbon atoms,
 an aryl or heteroaryl group, and an aralkyl or heteroaralkyl group, the alkyl group, which is linear or branched, of 1 to 4 carbon atoms, and m is an integer from 0 to 2 and n is an integer from 0 to 4.

36. A photochromic article comprising a polymeric binder and a naphthopyran represented by the general formula:

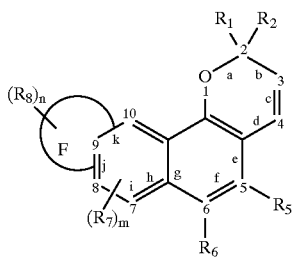

wherein $R_1$ and $R_2$ are the atoms or groups providing photochromic properties to the naphthopyran, and the ring group F comprises 5 ring atoms consisting of C and O and the ring group F comprises 5 ring atoms consisting of C and O, and F is fused to the k side, $R_5$ and $R_6$ are selected from the group consisting of:
 a hydrogen,
 a halogen,
 a linear or branched alkyl group of 1 to 12 carbon atoms,
 a cycloalkyl group of 3 to 12 carbon atoms,
 a linear or branched alkoxy group of 1 to 12 carbon atoms,
 a linear or branched alkenyl or alkynyl group of 1–12 carbon atoms,
 a linear or branched alkenyloxy or alkynyloxy group of 1–12 carbon atoms,
 an aryl or heteroaryl group, and an aralkyl or heteroaralkyl group, the alkyl group, which is linear or branched, of 1 to 4 carbon atoms, and m is an integer from 0 to 2 and n is an integer from 0 to 4.

37. The photochromic article of claim 19 wherein F is selected from the group consisting of dihydrofuran, methylene-dioxino and ethylene-dioxino.

38. The photochromic article of claim 20 wherein F is selected from the group consisting of dihydrofuran, methylene-dioxino and ethylene-dioxino.

39. The photochromic article of claim 21 wherein F is selected from the group consisting of dihydrofuran, methylene-dioxino and ethylene-dioxino.

40. The photochromic article of claim 31 wherein F is selected from the group consisting of dihydrofuran, methylene-dioxino and ethylene-dioxino.

41. The photochromic article of claim 32 wherein F is selected from the group consisting of dihydrofuran, methylene-dioxino and ethylene-dioxino.

42. The photochromic article of claim 33 wherein F is selected from the group consisting of dihydrofuran, methylene-dioxino and ethylene-dioxino.

43. The photochromic article of claim 34 wherein F is selected from the group consisting of dihydrofuran, methylene-dioxino and ethylene-dioxino.

44. The photochromic article of claim 35 wherein F is selected from the group consisting of dihydrofuran, methylene-dioxino and ethylene-dioxino.

* * * * *